United States Patent
Amblard

(10) Patent No.: US 7,483,745 B2
(45) Date of Patent: *Jan. 27, 2009

(54) ADJUSTMENT OF THE ATRIAL SENSITIVITY IN AN ACTIVE IMPLANTABLE MEDICAL DEVICE SUCH AS CARDIAC PACEMAKER

(75) Inventor: Amel Amblard, Chatenay-Malabry (FR)

(73) Assignee: ELA Medical S.A.S., Montrouge (FR)

( * ) Notice: Subject to any disclaimer, the term of this patent is extended or adjusted under 35 U.S.C. 154(b) by 319 days.

This patent is subject to a terminal disclaimer.

(21) Appl. No.: 10/645,326

(22) Filed: Aug. 21, 2003

(65) Prior Publication Data

US 2004/0122480 A1    Jun. 24, 2004

(30) Foreign Application Priority Data

Aug. 21, 2002  (FR) .................................. 02 10458

(51) Int. Cl.
*A61N 1/362* (2006.01)
(52) U.S. Cl. ..................................... 607/28
(58) Field of Classification Search ............... 607/27, 607/28; 600/521
See application file for complete search history.

(56) References Cited

U.S. PATENT DOCUMENTS

| | | | |
|---|---|---|---|
| 5,312,451 A | 5/1994 | Limousin et al. | 607/15 |
| 5,318,594 A | 6/1994 | Limousin et al. | 607/9 |
| 6,129,745 A * | 10/2000 | Sun et al. | 607/27 |
| 6,195,584 B1 * | 2/2001 | Hill et al. | 607/28 |
| 6,339,723 B1 | 1/2002 | Sloman | 607/28 |
| 6,397,105 B1 | 5/2002 | Bouhour et al. | 607/9 |
| 6,418,343 B1 * | 7/2002 | Zhang et al. | 607/9 |

FOREIGN PATENT DOCUMENTS

EP    0 55 0 342 B1    6/1997

* cited by examiner

*Primary Examiner*—George R Evanisko
(74) *Attorney, Agent, or Firm*—Orrick Herrington & Sutcliffe, LLP

(57) ABSTRACT

An active implantable medical device, such as a double chamber pacemaker or defibrillator or cardiovertor, having an improved adjustment of atrial sensitivity and of atrial stimulation energy. This device includes control algorithms for suspecting a loss of atrial detection and/or atrial capture that operates by analysis of a sequence of detected stimulations and ventricular and atrial detections. The following conditions are detected: an absence of ventricular activity post-atrial stimulation; and/or a lengthening, beyond a given limit, of the atrio-ventricular conduction delay over a predetermined number of successive cardiac cycles; and/or an occurrence of an atrial detection consecutive to an atrial stimulation over a predetermined number of successive cardiac cycles; and/or a ventricular extrasystole; and/or reduction, below a given limit, of a delay between atrial stimulation and ventricular detection; and/or the passage of an atrial detection to an atrial stimulation with concomitant reduction, below a given limit, of the delay between atrial event and ventricular detection. The atrial detection threshold and/or the atrial stimulation energy are adjusted, preferably stepwise, according to the detected conditions to provide improved patient care.

27 Claims, 3 Drawing Sheets

FIRST CASE: MANAGEMENT OF LOSS OF ATRIAL CAPTURE OR OF AVB

SECOND CASE: MANAGEMENT OF LOSS OF ATRIAL CAPTURE OR OF AVB

THIRD CASE: MANAGEMENT OF LOSS OF ATRIAL CAPTURE OR OF AVB

**FIRST CASE: SUSPICION OF LOSS OF ATRIAL DETECTION
(VENTRICLE NOT PRECEDED BY ATRIAL AND NO RR ACCELERATION)**

**SECOND CASE: SUSPICION OF LOSS OF ATRIAL DETECTION
(REDUCTION OF AR DELAY)**

ADJUSTMENT OF THE ATRIAL SENSITIVITY IN AN ACTIVE IMPLANTABLE MEDICAL DEVICE SUCH AS CARDIAC PACEMAKER

RELATED APPLICATION

This application is related to copending and commonly assigned U.S. patent application Ser. No. 10/645,329 filed concurrently herewith in the name of Amel Amblard and entitled Adjustment of the Atrial Sensitivity and of the Atrial Stimulation Energy in an Active Implantable Medical Device Such As a Double Chamber Cardiac Pacemaker.

FIELD OF THE INVENTION

The present invention relates to active implantable medical devices as such devices are defined by the Jun. 20, 1990 directive 90/385/CEE of the Council of the European Communities, more particularly to devices such as cardiac pacemakers, defibrillators, cardiovertors, and/or multisite devices that are able to deliver to the heart low energy stimulation pulses for the treatment of disorders of the heartbeat rate. The present invention relates more particularly to such devices that include circuits for double chamber stimulation, and even more particularly to such devices that are capable of an automatic operating mode switching (also called "automatic mode commutation" or "AMC"), for example, as are described in EP-A-0 488 904 and its corresponding U.S. Pat. No. 5,318,594, and EP-A-1 048 322 and its corresponding U.S. Pat. No. 6,397,105 B1, all assigned commonly herewith to ELA Médical, Montrouge France.

BACKGROUND OF THE INVENTION

The quality of the detection of spontaneous cardiac signals and the quality of the capture of a stimulated cardiac event are essential to the effectiveness of the various analysis and control algorithms that are integrated into the implanted devices. Parameters are available for this purpose to allow the doctor to adjust the sensitivity of detection of spontaneous activity and the stimulation energy level necessary to stimulate a cardiac contraction (i.e., a capture) as best as possible. Nevertheless, the optimal values are likely to evolve according to clinical and/or mechanical circumstances (e.g., a micro-displacement of the cardiac probe that monitors cardiac activity and/or delivers the stimulation energy pulses or the effect of drugs), these variations being able to be paroxystic or permanent.

OBJECTS AND SUMMARY OF THE INVENTION

It is, therefore, an object of the invention to resolve these difficulties while improving the operation of the known devices.

More precisely, it is an object of the invention to improve the auto-adjustment of the sensitivity and the stimulation energy values, suitable to avoid inopportune and useless misadjustments of these parameters.

Broadly, the present invention concerns improved apparatus and signal processing methods that detect situations of atrial under-detection and loss of atrial capture, to be able to ensure the correct operation of the various algorithms operating the device.

One aspect of the invention is directed to a device that is equipped with an automatic mode commutation operation, in which the detection and correction of the defects of atrial capture or atrial under-detection are employed to avoid an inappropriate switching to operating in a conventional DDD mode. This avoids unnecessarily stimulating the ventricle, and thus mitigates the possible noxious effects, from the hemodynamic point of view, of delivering such an inappropriate therapy.

The type of device to which the invention applies is a preferably double chamber device as described, for example, in the EP-A-0 488 904 and U.S. Pat. No. 5,318,594 mentioned above, i.e., including, for example, circuits of a conventional design that are able to detect spontaneous atrial and ventricular events, able to deliver ventricular and atrial stimulation pulses, and a means for suspecting a loss of atrial detection and/or a loss of atrial capture, said suspecting means operating by an analysis of a sequence of detected ventricular and atrial stimulations and detections.

In a manner characteristic of the invention, the means for suspecting the loss of atrial detection and/or atrial capture are able to detect one or more, and preferably each, of the following conditions: (1) an absence of ventricular activity post-atrial stimulation, (2) a lengthening, beyond a given limit, of the atrio-ventricular conduction delay over a predetermined number of successive cardiac cycles, (3) an occurrence of an atrial detection consecutive to an atrial stimulation over a predetermined number of successive cardiac cycles, (4) a detection of a ventricular extrasystole, (5) a reduction, below a given limit, of the delay between an atrial stimulation and a ventricular detection, and (6) a passage of an atrial detection to an atrial stimulation with concomitant reduction, below a given limit, of the delay between the atrial event and the ventricular detection.

Advantageously, the suspecting means also is able to deliver an atrial counter-stimulation of relatively increased energy, in the event of an absence of ventricular activity post-atrial stimulation. This delivery may actually occur indirectly, that is, by controlling the appropriate stimulation circuit to deliver a stimulation pulse at the desired energy level as the counter-stimulation pulse.

Preferably, the suspecting means can similarly deliver an increase in the atrial stimulation energy, relative to an initial stimulation energy value, over the following cycles in the event of an absence of ventricular activity post atrial stimulation, and can restore the stimulation energy to its initial stimulation energy value in the event of a persistence of the lengthening of the atrio-ventricular conduction delay. In this case, the suspecting means can advantageously operate a readjustment at periodic intervals, to lower the stimulation energy level in the event of a disappearance of the lengthening of the atrio-ventricular conduction delay, and inhibit this readjustment in the event of an increase in the stimulation energy over a predetermined number of the consecutive periodic intervals.

Preferably, the suspecting means also can deliver an increase in the atrial stimulation energy, relative to an initial stimulation energy value, over the following cycles in the event of an atrial detection consecutive to an atrial stimulation over a predetermined number of successive cardiac cycles, and restore the stimulation energy to its initial stimulation energy value in the event of persistence of this detection. In this case, the suspecting means can advantageously operate a readjustment at periodic intervals, to lower the stimulation energy level value in the event of a disappearance of atrial detection consecutive to an atrial stimulation over a predetermined number of successive cardiac cycles, and inhibit this readjustment in the event of increase in the energy of stimulation energy over a predetermined number of the consecutive periodic intervals. The lowering may be done in stepwise decrements until the energy level returns to its initial stimulation energy level.

In addition, the suspecting means are advantageously able to control an increase in the sensitivity of atrial detection circuits, relative to an initial value, and to restore the atrial sensitivity to its initial value in the event of a return to an atrial stimulation inducing a nonpathological delay between atrial stimulation and ventricular detection.

BRIEF DESCRIPTION OF THE DRAWINGS

Further benefits, features and characteristics of the present invention will become apparent to a person of ordinary skill in the art in view of the following detailed description of a preferred embodiment of the invention, made with in reference to the annexed drawings, in which.

DETAILED DESCRIPTION OF THE INVENTION

Figure 6:
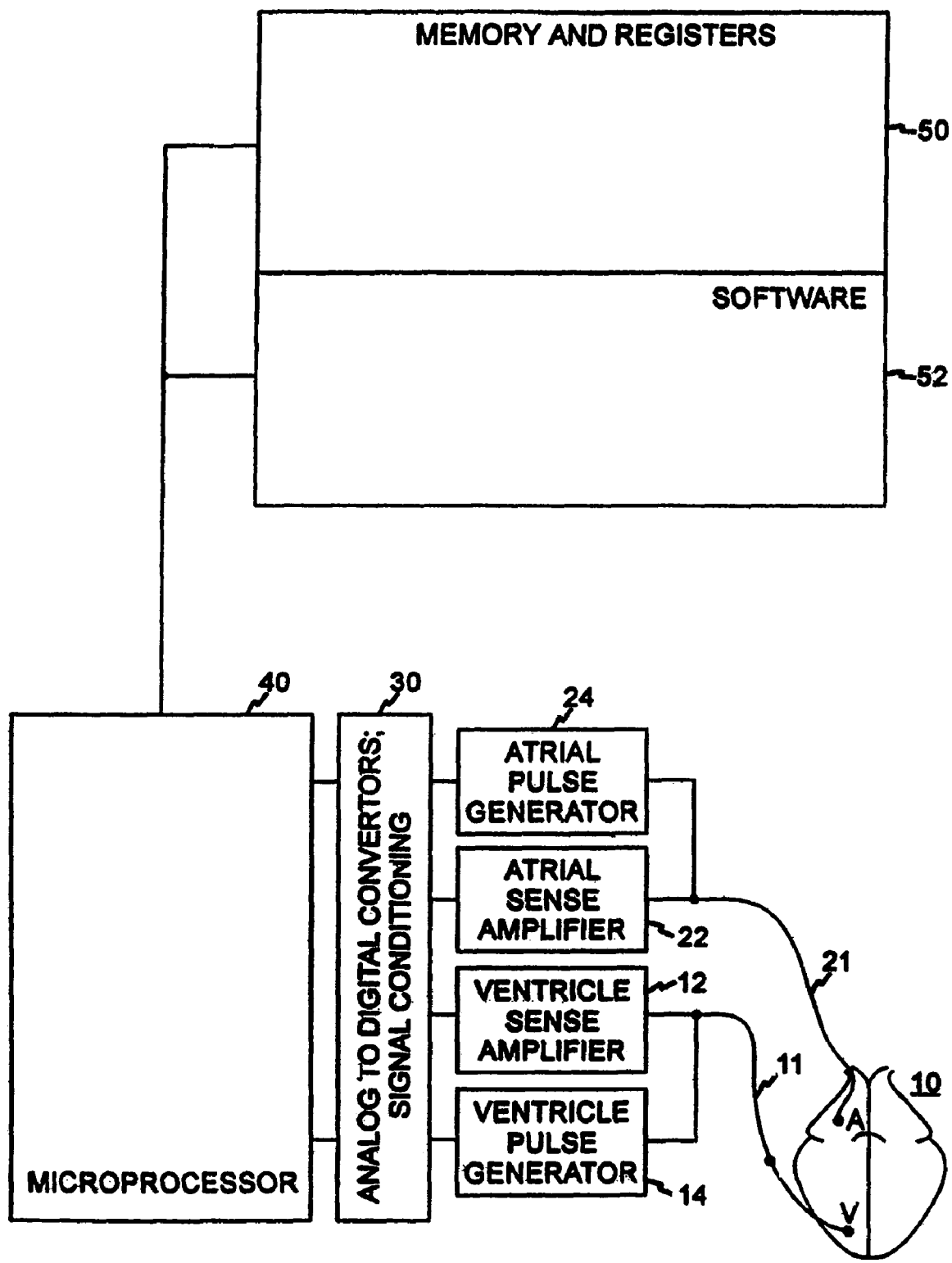
FIG. 6 is a schematic drawing of a device in accordance with the present invention.

With reference to FIG. 6, the invention can be preferably implemented by suitable programming of the control software 52 of a known microprocessor 40 controlled pacemaker having suitable memory and data registers 50, and signal conditioning input output circuits 30, the pacemaker being coupled to a heart 10 by cardiac lead(s) 11, 21 (two conventional bipolar leads shown). The control software also preferably integrates an automatic mode switching algorithm of the DDD-AMC type, such as that described by the aforementioned EP-A-0 488 904 and EP-A-1 048 322, and their respective corresponding U.S. Pat. Nos. 5,318,594 and 6,397,105 B1, which U.S. patents are incorporated herein by reference in their entirety as if fully set forth herein.

Preliminarily, the following definitions are used in the following description.

Detection P: sensing of a spontaneous activity having its origin in the atrium A (FIG. 6); it will be considered that there is indeed a detection P if an atrial detection is not followed in a given delay, for example, 31 ms, by a ventricular detection (otherwise, one would be in a situation of "ventricularfar-field" detection, i.e., a sensing via the atrium of a remote depolarization coming from the ventricle).

Detection R: sensing of a spontaneous activity having its origin in the ventricle V (FIG. 6).

Stimulation A: stimulation delivered in the atrium.

Stimulation V: stimulation delivered in the ventricle.

Atrial event: either detection P or stimulation A.

Ventricular event: either detection R or stimulation V.

Cardiac cycle: a delay separating two events of comparable nature in the same cavity, for example, separating two detections P, or two stimulations A.

PP average: an average interval of the atrial rate/rhythm, calculated, for example, over eight cardiac cycles not including an extrasystole.

Escape Interval (EI): the time interval, counted after a detection or a stimulation in a given cavity, following which a stimulation is delivered to the given cavity if no spontaneous event was detected in this given cavity. For the atrium, it is known as the atrial escape interval (AEI).

Atrial Extrasystole (AES): an atrial detection occurring inside the post-atrial atrial refractory period (PAARP), the calculation of this PAARP being that of the standard type DDD pacemaker.

Ventricular extrasystole (VES): a ventricular detection preceded by a ventricular detection or stimulation, with a coupling interval (R-R interval or V-R interval) less than or equal to a parametrable (i.e., a parameterized, programmable) value of the PP average, for example a value less than or equal to 75% of the PP average.

For further details on the detection and the treatment of the extrasystoles, one will be able to refer to the EP-A-0 550 342 and its corresponding U.S. Pat. No. 5,312,451 commonly assigned herewith to Ela Medical, which describes an algorithm for the detection and treatment of the VES by an asynchronous stimulation of the atrium and a controlled stimulation of the ventricle, which description is incorporated herein by reference.

In accordance with a preferred implementation of the invention employing an implanted device having a standard dual chamber cardiac pacing functionality, a certain number of functions, if they are present, are maintained just as they normally are. Thus, the algorithms for cardiac stimulation, the algorithm for "fallback" of the cardiac rate, and for prevention of electronic tachycardias (also referred to as PMT or Pacemaker-Mediated Tachycardia), and the algorithms that make it possible to calculate and apply PAARP periods and for protection against a retrograde conduction in the event of suspicion of VES are used in their known and conventional manners.

One now will discuss a way in which, in accordance with a preferred embodiment of the invention, the device includes the suspecting means manages the losses of atrial capture (or the atrio-ventricular blocks (AVB)), and those for which it manages the losses of atrial detection.

Figure 1:
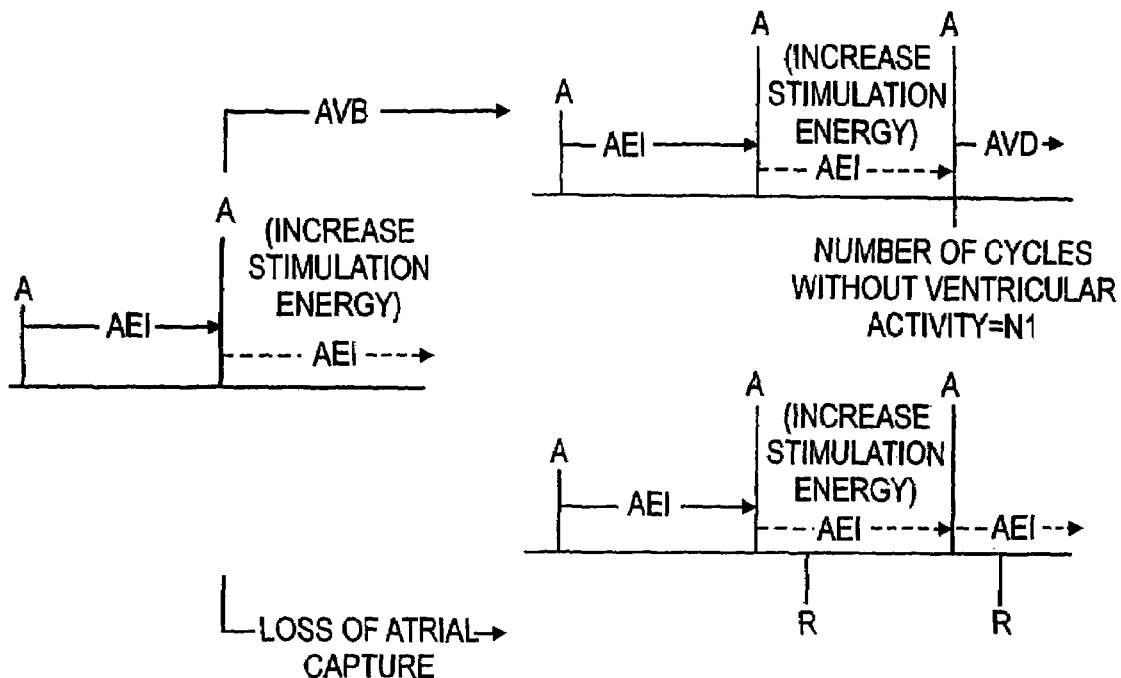
FIGS. 1 to 5 are chronograms corresponding to various operating modes of a device in accordance with the invention.

The management of the loss of capture is discussed with reference to the illustrated situations FIGS. 1 to 3. The First Case for management of loss of atrial capture corresponds to the situation illustrated on the chronogram of FIG. 1. This First Case is that of having detected and analyzed the sequence of spontaneous and stimulated events and identified an absence of ventricular activity after an atrial stimulation (this case being particular to a device that is equipped with automatic mode commutation). As a result, the device suspects a loss of atrial capture, and takes the following actions:

First, it applies an atrial counter-stimulation, provided that this function is activated by the physician (the delay separating the counter-stimulation from the preceding atrial stimulation being a programmable interval).

Next, the energy of the following atrial stimulation, or of the counter-stimulation, is increased. The value or level of energy applied is programmable and can be either the maximum energy permitted by the device, or an energy corresponding to a step (i.e., a programmable value) above the current energy. For example, it may be desirable in certain circumstances to use the maximum energy level, e.g., in the case of a counter-stimulation.

Two possibilities arise then: On the one hand, if the spontaneous ventricular activity (detection R) is restored (the lower chronogram of FIG. 1), then the device detects a normal behavior, without AVD, but with a stimulation energy increased to compensate for the risk of loss of capture.

On the other hand, (the upper chronogram of FIG. 1), if the authorized number of cycles N1 is reached without detecting ventricular activity, then any nonextrasystolic atrial event starts an AVD, and this is maintained during N2 cycles, or until the occurrence of a nonextrasystolic detection R. Preferably, N1=1 cycle, and N2=8 cycles. The maintenance of a detected condition over a number of cardiac cycles is known as persistence.

Figure 2:
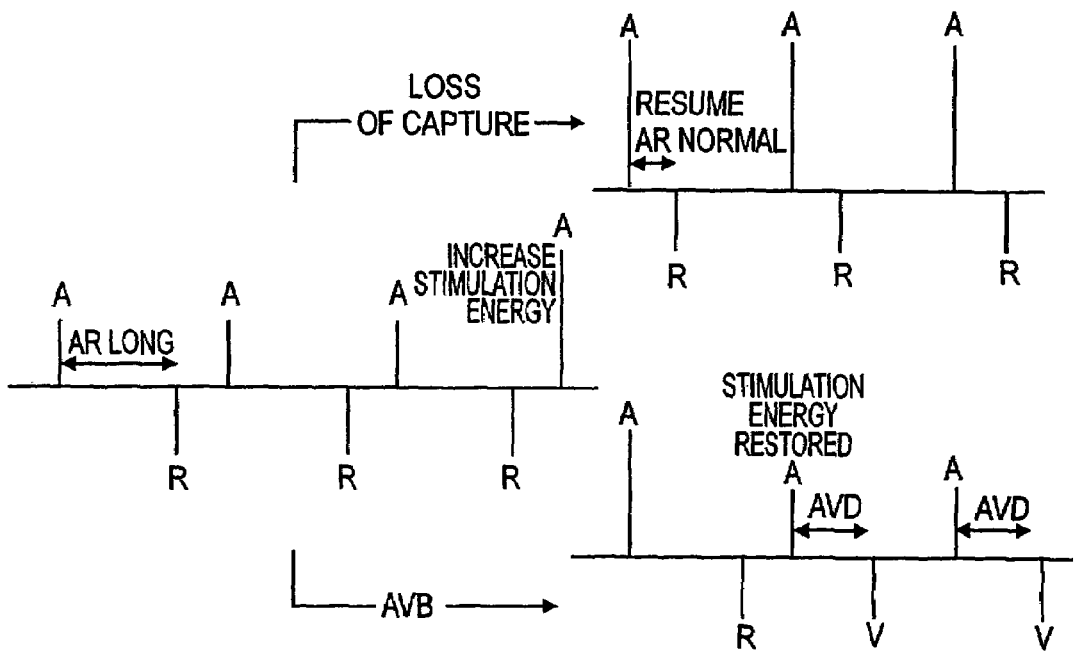

The Second Case of management of atrial loss of capture corresponds to the situation illustrated on the chronogram of FIG. 2. This case concerns the lengthening of the atrio-ventricular conduction delay over a given number of cycles N3, this number being programmable, for example, N3=3 cycles.

If the atrial activity is systematically a stimulated activity (Stimulation A), the device initially suspect a loss of atrial capture. In this case, the energy of the following stimulation is increased, with the parameterized value (maximum energy or an energy corresponding to a step above the current energy). Then, if the normal atrio-ventricular conduction delay is restored (the upper chronogram of FIG. 2), the device returns to its initial operation mode AAI, without AVD, with an increased stimulation energy.

In the contrary case the lower chronogram of FIG. 2, the initial atrial stimulation energy is restored, and a nonextrasystolic atrial event accordingly starts an AVD, which occurs during N2 successive cycles, or until the occurrence a nonextrasystolic detection R.

In the case that a lengthening of the atrio-ventricular conduction delay also is observed after an atrial detection, the device then can suspect the beginning an AVB and, at the end of N4 cycles, start an AVD, which continues during N2 successive cycles or until the occurrence of a nonextrasystolic detection R.

Figure 3:
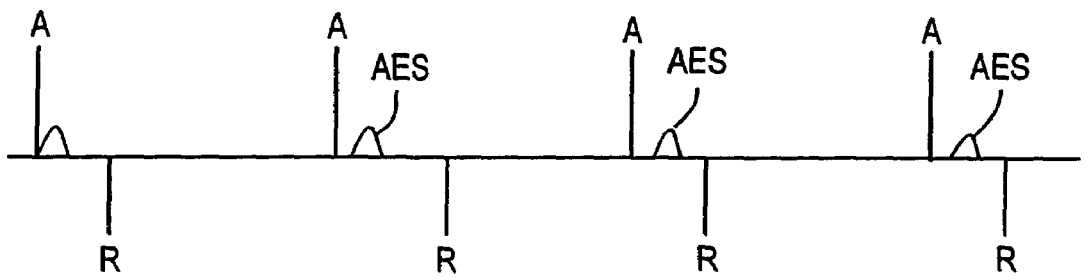

The Third Case of management of atrial loss of capture corresponds to the situation illustrated on the chronogram of FIG. 3. This Third Case is that of a sequence in which a stimulation A is followed by detection P of a P wave, which in turn is followed by the detection R of a spontaneous R wave, with this same sequence repeating itself over a programmable number of given cycles N4, for example, N4=3 cycles. This P wave, shifted in time from the stimulation A, sensed by the device, is considered to be an AES. The device suspects then a loss of atrial capture and increases the energy for the following stimulation to the parameterized value (maximum energy or energy corresponding to a step above current energy).

The device also has a functionality that enables it to restore the initial stimulation energy in the event of a temporary increase. In this regard, periodically, e.g., every 24 hours, the stimulation energy is lowered by a step. The step is preferably a programmable value and may be the same as the step increment, or not. Nevertheless, if an increase in energy occurs during 3 consecutive days, this "reversibility" is inhibited.

Figure 4:
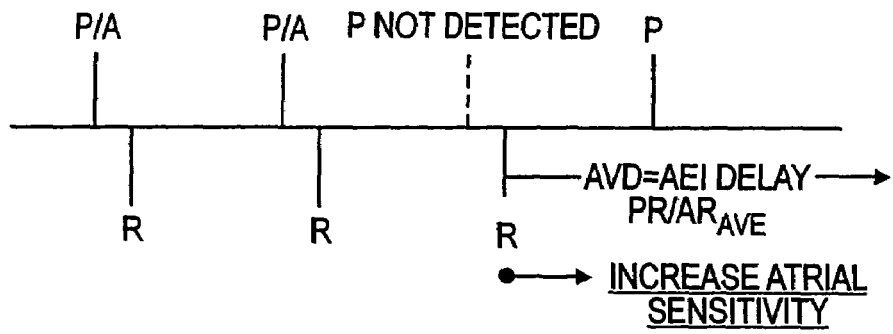
Figure 5:
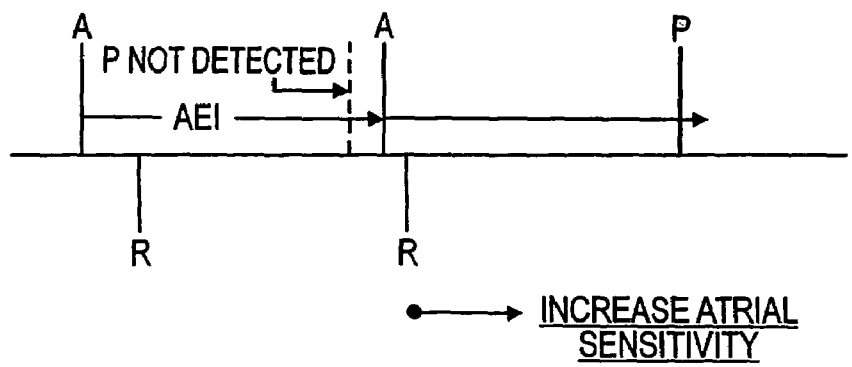

One now will describe the manner in which the device in accordance with a preferred embodiment of the invention manages a loss of atrial detection with reference to the illustrated chronograms of FIGS. 4 and 5.

The First Case of management of loss of atrial detection, illustrated in FIG. 4, is that of the detection of a ventricular event of a VES type, which one can assume is a loss of atrial detection if its coupling interval is higher than a programmed threshold value. In this First Case, the atrial sensitivity is increased (for example, the threshold applied to detect spontaneous activity (i.e., the detection threshold) is decreased by a step) until there is a return of a normal atrial detection, or a return to an atrial stimulation with a normal delay (i.e., in the absence of acceleration of the ventricular rate/rhythm between successive detections R) between atrial stimulation and ventricular detection.

The Second Case of management of atrial loss of detection corresponds to the situation illustrated on the chronogram of FIG. 5. If the delay between an atrial stimulation and a ventricular detection decreases by a quantity greater than one programmable duration, for example, 47 ms cycle to cycle, or compared to a delay defined as a normal delay, the device suspect a loss of atrial detection and increases the atrial sensitivity at the following cycle (for example, by decreasing the sensitivity threshold by a step) until the return of a normal delay between atrial stimulation and ventricular detection.

A Third Case of management of loss of atrial detection is that of the passage of a detection P to a stimulation A if the A-R delay is less than the P-R delay by a programmable duration (for example, 63 ms); the device suspect then also a loss of detection, and increases the sensitivity at the following cycle.

In the same manner as discussed for the stimulation energy, periodically, e.g., every 24 hours, the device decreases the sensitivity (by raising the detection threshold) to allow a return to the initial value. Nevertheless, if an increase in the sensitivity occurs during consecutive 3 days, this reversibility also is inhibited.

Suitable devices for which the present invention has application include, for example, the Talent™ and Symphony™, Rhapsody™ brand pacemakers and the Alto™ brand of defibrillators available from Ela Médical, Montrouge France. With reference also to FIG. 6, these devices are microprocessor based systems 40 having circuits (hardware and software) that provides for receiving, conditioning and processing detected electrical signals 30, and are capable of receiving software instructions 52 by telemetry (not shown), storing them in memory 50, and then executing those instructions to perform the functions and control algorithm described above in implementing the present invention. The creation of suitable software instructions 52 for controlling an implant to perform the aforementioned functions of the present invention are believed to be within the abilities of a person of ordinary skill in the art. The detection circuits 22 used to detect the cardiac signals in the atrium and the ventricle, in the left and/or right chambers, as well as the circuits 24 used to stimulate those chambers are well known and any suitable design may be used.

One skilled in the art will appreciate that the present invention can be practiced by other than the described embodiments, and the parameters provided with respect to numbers of cycles and time intervals are merely representative examples, which are presented for purposes of illustration and not of limitation.

I claim:

1. An active implantable medical device, comprising:
   circuit means for detecting spontaneous atrial and ventricular events;
   circuit means for providing ventricular and atrial stimulation; and
   means for automatic mode commutation;
   means for suspecting a loss of an atrial detection or capture, comprising means for determining a sequence of events having one or more of provided stimulations and detected ventricular and atrial events, and means for analyzing said sequence to detect a condition indicative of a suspected loss of atrial detection, wherein said analyzing means further comprises means for determining an occurrence of a ventricular extrasystole with a coupling interval that is greater than a programmed value, wherein said condition corresponds to one of said ventricular extrasystole being detected in the presence of said greater coupling interval and an occurrence of an atrial detection consecutive to an atrial stimulation over a predetermined number of successive cardiac cycles; and means for avoiding inappropriate switching to a DDD pacing mode when a condition indicative of a suspected loss of atrial detection is detected, comprising increasing means for increasing sensitivity after suspecting the loss of an atrial detection or capture.

2. The device of claim 1, wherein the detecting circuit means further comprises an initial atrial detection sensitivity, and the suspecting means further comprises means for increasing the atrial detection sensitivity in response to said detected condition.

3. The device of claim 2, further comprising means for stopping the increase of detection sensitivity in response to a detected return of normal atrial detection.

4. The device of claim 2, further comprising means for stopping the increase of detection sensitivity in response to a detected return to atrial stimulation with a normal delay between atrial stimulation and ventricular detection.

5. The device of claim 2, wherein the suspecting means further comprises means for restoring the atrial sensitivity to said initial atrial detection sensitivity in response to a detected atrial stimulation inducing a nonpathological delay between atrial stimulation and ventricular detection.

6. The device of claim 2, further comprising means for periodically decreasing the atrial detection sensitivity in response to the atrial detection sensitivity being greater than the initial atrial detection sensitivity.

7. The device of claim 6 further comprising means for inhibiting the periodically decreasing means from decreasing the atrial detection sensitivity in response to said increasing means increasing the atrial detection sensitivity during three consecutive days.

8. The device of claim 2, wherein the suspecting means further comprises means for detecting a delay between an atrial stimulation and a ventricular detection, and detecting a reduction of said delay below a given limit, wherein said condition further comprises said detected reduction.

9. The device of claim 8, further comprising means for stopping the increase of detection sensitivity in response to said detected delay corresponding to a normal delay.

10. The device of claim 8, wherein the suspecting means further comprises means for restoring the atrial sensitivity to said initial atrial detection sensitivity in response to a detected atrial stimulation inducing a nonpathological delay between atrial stimulation and ventricular detection.

11. The device of claim 2 wherein the suspecting means further comprises means for detecting a delay between an atrial event and a ventricular detection, and a passage from an atrial detection to an atrial stimulation with a concomitant reduction of said detected delay below a given limit, wherein said condition further comprises said passage.

12. The device of claim 11, further comprising means for stopping the increase of detection sensitivity in response to a detected return to atrial stimulation with a normal delay between atrial stimulation and ventricular detection.

13. The device of claim 11, wherein the suspecting means further comprises means for restoring the atrial sensitivity to said initial atrial detection sensitivity in response to a detected atrial stimulation inducing a nonpathological delay between atrial stimulation and ventricular detection.

14. An active implantable medical device, comprising:
circuit means for detecting spontaneous atrial and ventricular events;
circuit means for providing ventricular and atrial stimulation;
means for automatic mode commutation;
means for suspecting loss of an atrial detection, comprising means for determining a sequence of events having one or more of provided stimulations and detected ventricular and atrial events, and means for analyzing said sequence to detect a condition indicative of a suspected loss of atrial detection, wherein said analyzing means further comprises means for detecting a delay between an atrial stimulation and a ventricular detection and means for detecting a reduction of said delay below a given limit, wherein said condition further comprises said detected reduction; and
means for avoiding inappropriate switching to a DDD pacing mode when a condition indicative of a suspected loss of atrial detection is detected.

15. The device of claim 14, wherein the detecting circuit means further comprises an initial atrial detection sensitivity, and the suspecting means further comprises means for increasing the atrial detection sensitivity in response to said detected condition.

16. The device of claim 15, further comprising means for stopping the increase of detection sensitivity in response to a detected return of normal atrial detection.

17. The device of claim 15, further comprising means for stopping the increase of detection sensitivity in response to a detected return to atrial stimulation with a normal delay between atrial stimulation and ventricular detection.

18. The device of claim 15, wherein the suspecting means further comprises means for restoring the atrial sensitivity to said initial atrial detection sensitivity in response to a detected atrial stimulation inducing a nonpathological delay between atrial stimulation and ventricular detection.

19. The device of claim 15, further comprising means for periodically decreasing the atrial detection sensitivity in response to the atrial detection sensitivity being greater than the initial atrial detection sensitivity.

20. The device of claim 19 further comprising means for inhibiting the periodically decreasing means from decreasing the atrial detection sensitivity in response to said increasing means increasing the atrial detection sensitivity during three consecutive days.

21. An active implantable medical device, comprising:
circuit means for detecting spontaneous atrial and ventricular events;
circuit means for providing ventricular and atrial stimulation;
means for automatic mode commutation; and
means for suspecting loss of an atrial detection, comprising means for determining a sequence of events having one or more of provided stimulations and detected ventricular and atrial events, and means for analyzing said sequence to detect a condition indicative of a suspected loss of atrial detection in order to prevent inappropriate switching to a DDD pacing mode, wherein said analyzing means further comprises means for detecting a delay between an atrial event and a ventricular detection and means for detecting a passage from an atrial detection to an atrial stimulation with a concomitant reduction of said detected delay below a given limit, wherein said condition further comprises said passage.

22. The device of claim 21, wherein the detecting circuit means further comprises an initial atrial detection sensitivity, and the suspecting means further comprises means for increasing the atrial detection sensitivity in response to said detected condition.

23. The device of claim 22, further comprising means for stopping the increase of detection sensitivity in response to a detected return of normal atrial detection.

24. The device of claim 22, further comprising means for stopping the increase of detection sensitivity in response to a detected return to atrial stimulation with a normal delay between atrial stimulation and ventricular detection.

25. The device of claim 22, wherein the suspecting means further comprises means for restoring the atrial sensitivity to said initial atrial detection sensitivity in response to a detected atrial stimulation inducing a nonpathological delay between atrial stimulation and ventricular detection.

26. The device of claim 22, further comprising means for periodically decreasing the atrial detection sensitivity in response to the atrial detection sensitivity being greater than the initial atrial detection sensitivity.

27. The device of claim 26 further comprising means for inhibiting the periodically decreasing means from decreasing the atrial detection sensitivity in response to said increasing means increasing the atrial detection sensitivity during three consecutive days.

* * * * *